(12) United States Patent
Yamada et al.

(10) Patent No.: US 8,101,657 B2
(45) Date of Patent: Jan. 24, 2012

(54) PLANT DISEASE AND INSECT DAMAGE CONTROL COMPOSITION AND PLANT DISEASE AND INSECT DAMAGE PREVENTION METHOD

(75) Inventors: Eiichi Yamada, Chiba (JP); Ryutaro Ezaki, Yasu (JP); Hidenori Daido, Chiba (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 418 days.

(21) Appl. No.: 12/516,966

(22) PCT Filed: Nov. 22, 2007

(86) PCT No.: PCT/JP2007/072635
§ 371 (c)(1),
(2), (4) Date: May 29, 2009

(87) PCT Pub. No.: WO2008/065960
PCT Pub. Date: Jun. 5, 2008

(65) Prior Publication Data
US 2010/0071096 A1    Mar. 18, 2010

(30) Foreign Application Priority Data
Nov. 29, 2006  (JP) ................................ 2006-321404

(51) Int. Cl.
| A01N 43/08 | (2006.01) |
| A01N 43/80 | (2006.01) |
| A01N 43/653 | (2006.01) |
| A01N 41/06 | (2006.01) |

(52) U.S. Cl. ........ 514/471; 514/461; 514/380; 514/383; 514/604; 504/100

(58) Field of Classification Search .................. 514/461, 514/471, 380, 383, 604; 504/100
See application file for complete search history.

(56) References Cited

U.S. PATENT DOCUMENTS

| 5,532,365 A | 7/1996 | Kodaka et al. |
| 2004/0118040 A1* | 6/2004 | Asrar et al. ..................... 47/57.6 |
| 2005/0009703 A1 | 1/2005 | Wachendorff-Neumann et al. |
| 2006/0063829 A1 | 3/2006 | Andersch et al. |
| 2008/0171658 A1 | 7/2008 | Dyllick-Brenzinger et al. |
| 2008/0261811 A1 | 10/2008 | Krohn et al. |
| 2008/0274882 A1 | 11/2008 | Krohn et al. |
| 2010/0056594 A1 | 3/2010 | Sakurai et al. |

FOREIGN PATENT DOCUMENTS

| JP | 61-197553 A | 9/1986 |
| JP | 3-227904 A | 10/1991 |
| JP | 7-179448 A | 7/1995 |
| JP | 8-198710 A | 8/1996 |
| JP | 8-198713 A | 8/1996 |
| JP | 8-245322 A | 9/1996 |
| JP | 8-245323 A | 9/1996 |
| JP | 8-291009 A | 11/1996 |
| JP | 9-235282 A | 9/1997 |
| JP | 11-5708 A | 1/1999 |
| JP | 11-228309 A | 8/1999 |
| JP | 11-292715 A | 10/1999 |
| JP | 11-302107 A | 11/1999 |
| JP | 11-302108 A | 11/1999 |
| JP | 11-302109 A | 11/1999 |
| JP | 11-302110 A | 11/1999 |
| JP | 11-302111 A | 11/1999 |
| JP | 11-322511 A | 11/1999 |
| JP | 2001-72511 A | 3/2001 |
| JP | 2001-72512 A | 3/2001 |
| JP | 2001-72513 A | 3/2001 |
| JP | 2001-81003 A | 3/2001 |
| JP | 2004-538325 A | 12/2004 |
| JP | 2005-517714 A | 6/2005 |
| JP | 2006-213664 A | 8/2006 |
| WO | WO 2006/036827 A1 | 4/2006 |
| WO | WO 2006/069654 A2 | 7/2006 |
| WO | WO 2006/069655 A1 | 7/2006 |
| WO | WO 2006/082723 A1 | 8/2006 |
| WO | WO 2006/094978 | 9/2006 |
| WO | WO 2007/010036 A2 | 1/2007 |
| WO | WO 2008/003738 | 1/2008 |

OTHER PUBLICATIONS

Webster's New World Dictionary, 2nd college ed., The World Publishing Co., NY, entry for "prevent," p. 1127 (1972).
Derwent abstract 2006-573208; abstracting JP 2006-213664 (Aug. 2006).
Machine translation of JP 2006-213664 (Aug. 2006).
Translation of JP 2006-213664 (Aug. 2006).
International Search Report (PCT/ISA/210) dated Jan. 8, 2008.
Written Opinion (PCT/ISA/237) dated Jan. 8, 2008.
International Search Report (PCT/ISA/210) dated Jan. 7, 2008.
Written Opinion (PCT/ISA/237) dated Jan. 7, 2008.

* cited by examiner

*Primary Examiner* — John Pak
(74) *Attorney, Agent, or Firm* — Buchanan Ingersoll & Rooney PC

(57) ABSTRACT

The invention provides a plant disease and insect damage control composition including, as active ingredients, dinotefuran and at least one fungicidal compound; and a plant disease and insect damage prevention method that includes applying such a composition to a plant body, soil, plant seed, stored cereal, stored legume, stored fruit, stored vegetable, silage, stored flowering plant, or export/import timber. The invention provides a new plant disease and insect damage control composition and a plant disease and insect damage prevention method with very low toxicity to mammals and fishes, the composition and method showing an effect against plural pathogens and pest insects, including emerging resistant pathogens and resistant pest insect, by application to a plant body, soil, plant seed, stored cereal, stored legume, stored fruit, stored vegetable, silage, stored flowering plant, or export/import timber.

11 Claims, No Drawings

PLANT DISEASE AND INSECT DAMAGE CONTROL COMPOSITION AND PLANT DISEASE AND INSECT DAMAGE PREVENTION METHOD

FIELD OF THE INVENTION

The present invention relates to a plant disease and insect damage control composition and a plant disease and insect damage prevention method.

BACKGROUND OF THE INVENTION

It is described in Japanese Patent Application Laid-Open (JP-A) No. 07-179448 that an effect is shown by dinotefuran as an insecticidal compound, with application methods such as foliar application and water application, against: Lepidopterous pests, such as the common cutworm, Chilo and the common cabbageworm; Hemiptera pests, such as the greenhouse white fly, the cotton aphid, the comstock mealybug, and the southern green stink bug; Coleoptera pests, such as the rice water weevil and the striped flea beetle; Diptera pests such as the house fly and the rice leaf miner; Thysanoptera pests such as onion thrips; Orthoptera pests, such as the smoky brown cockroach and rice grasshopper; and the like. However, there are no indication that there is an effect shown for pest insect prevention by application procedures such as spray treatment, coating treatment, dip treatment, dressing treatment, fumigation and smoking treatment, and pressure injection to plant seeds.

Moreover, it is described in JP-A No. 08-245322, JP-A No. 08-245323, JP-A No. 08-291009, and JP-A No. 11-005708 that a composition containing dinotefuran and a fungicidal compound shows, in the field of paddy rice cultivation, a synergistic effect against rice blast disease (*Pyricularia oryzae*) and sheath blight disease (*Rhizoctonia solani*) in application methods such as to seedling raising boxes. However, there is no indication that an effect is shown in disease prevention and insect damage prevention by applications of spray treatment, coating treatment, dip treatment, or dressing treatment to plant seeds. Furthermore, there is no indication of the use of mixtures of fulsulfamide and/or hymexazol, with dinotefuran, nor is there any indication of a synergistic effect due to mixed use.

It is described in JP-A 61-197553 (Japanese Patent Announcement No. 06-027113) that flusulfamide, as a fungicidal compound, shows antimicrobial activity or growth inhibition activity to various plant pathogenic microbes across a wide range of plant diseases by spraying, soil surface application, soil incorporation application, seed dipping, and root dust coating, root immersion of seedlings and the like, and flusulfamide shows a prominent effect especially against soil diseases where the number of effective control chemicals are small. Furthermore, the above document mentions the possibility of concomitant use of flusulfamide with a pesticide and the like. However, there is no indication of using flusulfamide with dinotefuran or hymexazol, or a synergistic effect thereof.

JP-A No. 03-227904 (Japanese Patent No. 2,860,492) and JP-A No. 08-198710 (Japanese Patent No. 3,608,830), and JP-A No. 08-198713 (Japanese Patent No. 3,608,831) disclose a synergistic effect of the concomitant use of flusulfamide with a fungicidal compound, and the like. However, there is no indication of using flusulfamide with dinotefuran.

As chemicals which prevent plant disease by applying to plant seeds there are, conventionally, benomyl agents, thiophanate-methyl agents, prochloraz agents, pefurazoate agents, and the like, and it is known that these will demonstrate an effect, as single agents or mixtures thereof, by spray treatment, coating treatment, dip treatment, or dressing treatment to seeds. How ever, among these agents, it is reported that the control effect against rice bakanae disease of benomyl and thiophanate-methyl agents is falling. Moreover, while prochloraz agents are applied against rice blast disease, brown spot, bakanae disease, tulip bulb rot, and shallot dry rot disease, and pefurazoate agents are applied against rice blast disease, brown spot, bakanae disease, wheat pink snow mold, and tulip bulb rot, other applications of there agents are not known. Moreover, mixtures of benomyl and thiuram are applied for: rice diseases of rice blast disease, seedling blight, bakanae disease, brown spot, bacterial grain rot, bacterial brown stripe and discolorations of rice; wheat-like cereal diseases of barley stripe, loose smut, Cephalosporium stripe and scald; cucumber fusarium wilt; gummy stem blight; damping off; tomato fusarium wilt; watermelon fusarium wilt; soya bean purple seed stain; taros Alternaria leaf spot; sugarcane smut; Coix lacryma-jobi leaf blight; smut; corn seedling blight; Japanese pumpkin fusarium basal rot; shallots dry rot disease; garlic white rot; and yam root rot. However, other applications thereof are not known. Moreover, since mixtures of benomyl and thiuram have a strong affect on aquatic animals, there are warnings against their use in places where there is a possibility of dispersal or flow into rivers, lakes, coastal areas, and culture ponds.

DESCRIPTION OF THE INVENTION

Problem to be Solved by the Invention

An object of the invention is to provide a new prevention composition and control method against disease and pest damage to plant bodies, soil, plant seeds, stored cereals, stored legumes, stored fruits, stored vegetable, silage, stored flowering plants and export/import timber, wherein the prevention composition and control method show an effect against plural pathogens and pest insects, including emerging resistant pathogens and resistant pest insects, yet have a very low toxicity to mammals and fish, the composition being applied to the plant body, soil, plant seeds, stored cereals, stored legumes, stored fruits, stored vegetable, silage, stored flowering plants and export/import timber.

Means for Solving the Problem

As a result of carrying out diligent examination and investigation, the present inventors have determined that a composition in which at least one sort of fungicidal compound is added to dinotefuran shows a high preventive effect at a low dose to plural types of disease damage and insect damage, and shows a stable preventive effect toward the above resistant pathogens and/or resistant pest insects, resulting of the invention.

That is, the means for solving problem is as follows.

1. A plant disease and insect damage control composition comprising active ingredients of (RS)-1-methyl-2-nitro-3-(tetrahydro-3-furylmethyl)guanidine (common name: dinotefuran) and at least one fungicidal compound selected from the group consisting of 2',4-dichloro-α,α,α-trifluoro-4'-nitro-m-toluenesulfonanilide (common name: flusulfamide), 3-hydroxy-5-methylisoxazol (common name: hymexazol), and (RS)-2-(4-fluorophenyl)-1-(1H-1,2,4-triazol-1-yl)-3-(trimethylsilyl)propan-2-ol (common name: simeconazole).

2. The plant disease and insect damage control composition according to claim 1, wherein the at least one fungicidal compound comprises 2',4-dichloro-α,α,α-trifluoro-4'-nitro-m-toluenesulfonanilide (common name: flusulfamide).
3. The plant disease and insect damage control composition according to claim 1, wherein the at least one fungicidal compound comprises 3-hydroxy-5-methylisoxazol (common name: hymexazol).
4. The plant disease and insect damage control composition according to claim 1, wherein the at least one fungicidal compound comprises (RS)-2-(4-fluorophenyl)-1-(1H-1,2,4-triazol-1-yl)-3-(trimethylsilyl)propan-2-ol (common name: simeconazole).
5. The plant disease and insect damage control composition according to claim 1, wherein the at least one fungicidal compound comprises a mixed composition of at least two selected from the group consisting of flusulfamide, hymexazol, and simeconazole.
6. A plant disease and insect damage prevention method comprising applying the pest control composition according to claim 1 to a plant body, soil, plant seed, stored cereal, stored legume, stored fruit, stored vegetable, silage, stored flowering plant, or export/import timber.
7. The plant disease and insect damage prevention method according to claim 6, wherein the method of application to plant seeds is spray treatment, coating treatment, dip treatment, or dressing treatment of seeds.
8. The plant disease and insect damage prevention method according to claim 6, wherein the method of application to a stored cereal, stored legume, stored fruit, stored vegetable, silage, stored flowering plants, or export/import timber is spray treatment, coating treatment, dip treatment, dressing treatment, fumigation treatment, smoke treatment, or pressure injection.
9. Plant seed, stored cereal, stored legume, stored fruit, stored vegetable, silage, stored flowering plant, or export/import timber to which the plant disease and insect damage control composition according to claim 1 has been applied.
10. The plant disease and insect damage prevention method according to claim 6, wherein the method of application to a plant body or soil is foliar application to a plant body, spray treatment to the soil surface, soil incorporation after spray treatment to the soil surface, injection treatment into the soil, or soil drenching treatment.
11. A method of preventing plant disease and insect damage to a plant body grown from a plant seed, the method comprising applying, to the plant seed, the plant disease and insect damage control composition according to claim 1.

Effect of the Invention

The method of the invention, while demonstrating a high preventive effect to disease damage and insect damage generated in plant bodies, soil, plant seeds, stored cereals, stored legumes, stored fruits, stored vegetables, silage, stored flowering plants, and export/import timber, also shows a stable preventive effect to microbe pathogens and pest insects that are resistant to existing chemicals.

BEST MODE OF CARRYING OUT THE INVENTION

Specific examples of the types of disease damage which may be prevented with the method of the invention include, but are not limited to, the following:

rice diseases such as rice blast disease (*Pyricularia oryzae*), brown spot (*Cochliobolus miyabeanus*), bakanae disease (*Gibberella fujikuroi*);

wheat-like cereal diseases such as barley stripe (*Pyrenophora graminea*), loose smut (*Ustilago nuda, Ustilago tritici, Ustilago nigra, Ustilago avenae*), bunts (*Tilletia caries, Tilletia pancicii*), covered smut (*Ustilago hordei, Ustilago kolleli*), scald (*Rhynchosporium secalis*), Septoria tritici leaf blotch (*Septoria tritici*), glume blotch (*Leptosphaeria nodorum*), pink snow mold (*Microdochium nivale*), Fusarium head blight (*Fusarium graminearum, Fusarium culmorum, Fusarium avenaceum, Microdochium nivale*), kernel blight (*Helminthosporium sativum*), take-all (*Gaeumannomyces graminis*), Cephalosporium stripe (*Cephalosporium gramineum*) and net blotch (*Dreschlera teres*);

corn diseases such as common smut (*Ustilago mydis*);

legume diseases such as seedling blight (*Rhizoctionia solani*) and Sclerotinia stem rot (*Sclerothinia sclerotorium*), purple seed stain of soya beans (*Cercospora kikuchii*) and Rhizoctonia root rot (*Rhizoctonia solani*);

diseases in sugar beet such as root rot (*Rhizotconia solani*);

rape diseases such as black leg (*Leptosphaeria maculans*), alternaria leaf spot (*Alternaria brassicae*);

damping off (*Rhizoctonia solani*) of various vegetables, such as tomato, cucumber, Japanese radish, watermelon, eggplant, sweet pepper, and spinach; and diseases such as tomato wilt (*Fusarium oxysporum*), cucurbitaceae Fusarium wilt (*Fusarium oxysporum*), cabbage yellows (*Fusarium oxysporum*), cauliflower chlorosis (*Fusarium oxysporum*), and Chinese cabbage Verticillium wilt (*Verticillium dahlie*).

Examples that may be given of the insect damage which can be prevented include, but are not limited to, the following from the order of grasshoppers, crickets and locusts Examples that may be given of the insect damage which can be prevented include, but are not limited to, the following from the order of grasshoppers, crickets and locusts (Orthoptera):

BLATTIDAE such as the American cockroach (*Periplaneta americana*), the smokybrown cockroach (*Periplaneta fuliginosa*), the Japanese cockroach (*Periplaneta japonica*);

BLATTELLIDAE such as the German cockroach (*Blattella germanica*), the false German cockroach (*Blattella lituricollis*);

TETTIGONIIDAE such as the northern rice katydid (*Homorocoryphus jezoensis*), the northern rice katydid (*Homorocoryphus lineosus*);

GRYLLOTALPIDAE such as the mole crickets (*Gryllotalpa* sp.); and

ACRIDIDAE such as the short-horned grasshoppers (*Oxya hyla intricata*) and rice grasshopper (*Oxya yezoensis*);

the following from the order of Termites/White Ants (ISOPTERA): the dry-wood termite (*Cryptotermes domesticus*), the Formosan subterranean termite (*Coptotermes formosanus*), the Japanese subterranean termite (*Reticulitermes speratus*), the macrotermitine termite (*Odontotermes formosanus*);

the following from the order of thrips (THYSANOPTERA):

THRIPIDAE such as the grass thrips (*Anaphothrips obscurus*), the cocksfoot thrips (*Chirothrips manicatus*), the chanokuro-azamiuma (*Dendrothrips minowai*), the flower thrips (*Frankliniella intonsa*), the yurikiiro-azamiuma (*Frankliniella lilivora*), the greenhouse thrips (*Heliothrips haemorrhoidalis*), the composite thrips (*Microcephalothrips abdominalis*), the oriental soybean thrips (*Mycterothrips glycines*), the mulberry thrips (*Pseudodendrothrips mori*), the yellow tea thrips (*Scirtothrips dorsalis*), the redbanded (*Selenothrips rubrocinctus*), the oriental rice thrips (*Stenchaetothrips biformis*), the negikuro-azamiuma (*Thrips alliorum*), the loquat thrips (*Thrips coloratus*), the honeysuckle thrips (*Thrips flavus*), the Hawaiian flower thrips (*Thrips hawaiiensis*), the chrysanthemum thrips (*Thrips nigropilosus*), the melon thrips (*Thrips palmi*), the western flower thrips (*Frankliniella occidentalis*), the Japanese flower thrips (*Thrips setosus*), the gladiolus thrips (*Thrips simplex*), the onion thrips (*Thrips tabaci*);

PHLAEOTHRIPIDAE such as the rice aculeated thrips (*Haplothrips aculeatus*), the Chinese thrips (*Haplothrips chinensis*), the hana-kudaazamiuma (*Haplothrips kurdjumovi*), the red clover thrips (*Haplothrips niger*), the shiionaga-kudaazamiuma (*Leeuwania pasanii*), the camphor thrips (*Liothrips floridensis*), the lily thrips (*Liothrips vaneeckei*), the thrip (*Litotetothrips pasaniae*), the Japanese gall-forming thrips (*Ponticulothrips diospyrosi*);

the following from the order of the true bugs (HEMIPTERA): PENTATOMIDAE such as the purple stink bug (*Carpocoris purpureipennis*), the sloe bug (*Dolycoris baccarum*), the painted bug (*Eurydema pulchrum*), the cabbage bug (*Eurydema rugosum*), the Two-spotted sesame bug (*Eysarcoris guttiger*), the ootogeshirahoshi-kamemushi (*Eysarcoris lewisi*), the white spotted spined stink bug (*Eysarcoris parvus*), the shield bug (*Eysarcoris ventralis*), the polished green stink bug (*Glaucias subpunctatus*), the red-striped stink bug (*Graphosoma rubrolineatum*), the brown malmorated stink bug (*Halyomorpha mista*), the rice stink bug (*Lagynotomus elongatus*), the oriental green stink bug (*Nezara antennata*), the southern green stink bug (*Nezara viridula*), the redbanded shield bug (*Piezodorus hybneri*), the brown-winged green bugs (*Plautia stali*), the black rice bug (*Scotinophara lurida*), the brown rice stink bug (*Starioides degenerus*);

COREIDAE such as the winter cherry bug (*Acanthocoris sordidus*), the Coreid-hug (*Anacanthocoris striicornis*), the rice stink bug (*Cletus punctiger*), the slender rice bug (*Cletus trigonus*), the Leaf-Footed Bug (*Molipteryx fuliginosa*);

ALYDIDAE such as the paddy bug (*Leptocorisa acuta*), the rice bug (*Leptocorisa chinensis*), the rice bug (*Leptocorisa oratorius*), the bean bug (*Riptortus clavatus*);

RHOPALIDAE such as the carrot bug (*Aeschynteles maculatus*), the hyaline grass bug (*Liorhyssus hyalinus*);

LYGAEIDAE such as the oriental chinch bug (*Cavelerius saccharivorus*), the bamboo chinch bug (*Macropes obnubilus*), the hiratahyoutan-nagakamemushi (*Pachybrachius luridus*), the kuroashihoso-nagakamemushi (*Paromius jejunus*), the seed bug (*Togo hemipterus*);

PYRRHOCORIDAE such as the cotton bug (*Dysdercus cingulatus*), the small cotton bug (*Dysdercus poecilus*);

TINGIDAE such as the chrysanthemum lace bug (*Galeatus spinifrons*), the yanagi-gunbai (*Metasalis populi*), the camphor lace bug (*Stephanitis fasciicarina*), the pear lace bug (*Stephanitis nashi*), the azalea lace bug (*Stephanitis pyrioides*), the chestnut lace bug (*Uhlerites debile*), the walnut lace bug (*Uhlerites latiorus*);

MIRIDAE such as the alfalfa plant bug (*Adelphocoris lineolatus*), the buchihigekuro-kasumikame (*Adelphocoris triannulatus*), the koao-kasumikame (*Apolygus lucorum*), the pale green plant bug (*Apolygus spinolai*), the akahoshi-kasumikame (*Creontiades coloripes*), the tobacco leaf bug (*Nesisiocoris tenuis*), the Japanese garden fleahopper (*Ectometopterus micantulus*), the oriental garden fleahopper (*Halticiellus insularis*), the apple leaf bug (*Heterocordylus flavipes*), the Japanese tarnished plant bug (*Lygus disponsi*), the madara-kasumikame (*Cyphodemidea saundersi*), the sugarbeet leaf bug (*orthotylus flavosparsus*), the wheat leaf bug (*Stenodema calcaratum*), the timothy grass bug (*Stenotus binotatus*), the sorghum plant bug (*Stenotus rubrovittatus*), the brokenbacked bug (*Taylorilygus pallidulus*), the rice leaf bug (*Trigonotylus coelestialium*);

CICADIDAE such as the large brown cicada (*Graptopsaltria nigrofuscata*);

APHROPHORIDAE such as the maeki-awafuki (*Aphrophora costalis*), the pine froghopper (*Aphrophora flavipes*), the common spittlebug (*Aphrophora intermedia*), the himefutatennaga-awafuki (*Clovia punctata*), the meadow spittlebug (*Philaenus spumarius*);

TETTIGELLIDAE such as the black-tipped leafhopper (*Bothrogonia japonica*), the green leafhopper (*Cicadella viridis*);

CICADELLIDAE such as the oak leafhopper (*Aguriahana quercus*), the polyphagous leafhopper (*Alnetoidia alneti*), the citrus leafhopper (*Apheliona ferruginea*), the grape Leafhopper (*Arboridia apicalis*), the small green leafhopper (*Edwardsiana flavescens*), the rose leafhopper (*Edwardsiana rosae*), the pine leafhopper (*Empoasca abietis*), the tea green leafhopper (*Empoasca onukii*), the orange headed leafhopper (*Thaia subrufa*), the smaller citrus leafhopper (*Zyginella citri*);

DELTOCEPHALIDAE such as aster leafhopper (*Macrosteles fascifrons*), the green rice leafhopper (*Nephotettix cincticeps*), the green rice leafhopper (*Nephotettix nigropictus*), the green rice leafhopper (*Nephotettix virescens*), the apple leafhopper (*Orientus ishidai*), the zig-zag rice leafhopper (*Recilia dorsalis*), the wheat leafhopper (*Sorhoanus tritici*), the alder leafhopper (*Speudotettix subfusculus*);

DELPHACIDAE such as the small brown planthopper (*Laodelphax striatellus*), the brown planthopper (*Nilaparvata lugens*), the pale sugarcane planthopper (*Numata muiri*), the maize planthopper (*Peregrinus maidis*), the sugarcane leafhopper (*Perkinsiella saccharicida*), the white-backed planthopper (*Sogatella furcifera*), the panicum planthopper (*Sogatella panicicola*);

PSYLLIDAE such as the mulberry sucker (*Anomomeura mori*), the lacquer psylla (*Calophya nigridorsalis*), the citrus psylla (*Diaphorina citri*), the hibiscus psylla (*Mesohomotoma camphorae*), the abies psylla (*Psylla abieti*), the Plant louse (*Psylla alni*), the sins psylla (*Acizzia jamatonica*), the apple sucker (*Cacopsylla mali*), the black apple sucker (*Psylla malivorella*), the pear sucker (*Psylla pyrisuga*), the tobira psylla (*Psylla tobirae*), the camphor sucker (*Trioza camphorae*), the guercus sucker (*Trioza quercicola*);

ALEYRODIDAE such as the orange spiny whitefly (*Aleurocanthus spiniferus*), the grape whitefly (*Aleurolobus taonabae*), the tobacco whitefly (*Bemisia tabaci*), the citrus whitefly (*Dialeurodes citri*), the greenhouse whitefly (*Trialeurodes vaporariorum*), the silverleaf whitefly (*Bemisia argentifolii*);

PHYLLOXERIDAE such as the vine phylloxera (*Viteus vitifolii*);

PEMPHIGIDAE such as the root aphid (*Aphidounguis mali*), the woolly aphid (*Eriosoma lanigerum*), the sugarcane root aphid (*Geoica lucifuga*);

APHIDIDAE such as the pea aphid (*Acyrthosiphon pisum*), the spirea aphid (*Aphis citricola*), the cowpea aphid (*Aphis craccivora*), the yanabi-aburamushi (*Aphis farinosa yanagicola*), the cotton aphid (*Aphis gossypii*), the foxglove aphid (*Aulacorthum solani*), the leafcurl plum aphid (*Brachycaudus helichrysi*), the cabbage aphid (*Brevicoryne brassicae*), the tulip bulb aphid (*Dysaphis tulipae*), the European birch aphid (*Euceraphis punctipennis*), the mealy plum aphid (*Hyalopterus pruni*), the turnip aphid (*Lipaphis erysimi*), the chrysanthemum aphid (*Macrosiphoniella sanborni*), the potato aphid (*Macrosiphum euphorbiae*), the bean aphid (*Megoura crassicauda*), the nashikofuki-aburamushi (*Melanaphis siphonella*), the apple leafcurling aphid (*Myzus malisuctus*), the umekobu-aburamushi (*Myzus mumecola*), the green peach aphid (*Myzus persicae*), the onion aphid (*Neotoxoptera formosana*), the apple aphid (*Ovatus malicolens*), the waterlily aphid (*Rhopalosiphum nymphaeae*), the bird-cherry aphid (*Rhopalosiphum padi*), the rice root aphid (*Rhopalosophum rufiabdominalis*), the root aphid (*Sappaphis piri*), the pear aphid (*Schizaphis piricola*), the gain aphid (*Sitobion akebiae*), the ibarahigenaga-aburamushi (*Sitobion ibarae*), the tea aphid (*Toxoptera aurantii*), the brown citrus aphid (*Toxoptera citricidus*), the peach aphid (*Tuberocephalus momonis*), the taiwanhigenaga-aburamushi (*Uroleucon formosanum*);

MARGARODIDAE such as the giant mealy bug (*Drosicha corpulenta*), the cottony cushion scale (*Icerya purchasi*);

PSEUDOCOCCIDAE such as the matsumoto mealybug (*Crisicoccus matsumotoi*), the Kuwana Pine Mealybug (*Crisicoccus pini*), the Taxus mealybug (*Dysmicoccus wistariae*), the citrus mealybug (*Planococcus citri*), the Japanese mealybug, the (*Planococcus kranuhiae*), the citrus mealybug (*Pseudococcus citriculus*), the comstock mealybug (*Pseudococcus comstocki*);

COCCIDAE such as the Indian wax scale (*Ceroplastes ceriferus*), the red wax scale (*Ceroplastes rubens*), the mikan-hiratakaigaramushi (*Coccus discrepans*), the brown soft scale (*Coccus hesperidum*), the citricola scale (*Coccus pseudomagnoliarum*), the Chinese wax scale (*Ericerus pela*), the European fruit lecanium scale (*Lecanium corni*), the Europian peach scale (*Lecanium persicae*), the citrus cottony scale (*Pulvinaria aurantii*), the soft scale (*Pulvinaria citricola*), the cottony mulberry scale (*Pulvinaria kuwacola*);

DIASPIDIDAE such as the kankitsu-kaigaramushi (*Andaspis kashicola*), the California red scale (*Aonidiella aurantii*), the yellow scale (*Aonidiella citrina*), the coconut scale (*Aspidiotus destructor*), the oleander scale (*Aspidiotus hederae*), the circular black scale (*Chrysomphalus ficus*), the San Jose scale (*Comstockaspis perniciosa*), the camellia mining scale (*Duplaspidiotus claviger*), the purple scale (*Lepidosaphes beckii*), the oystershell scale (*Lepidosaphes ulmi*), the Japanese maple scale (*Lepidosaphes japonica*), the scale (*Parlatoreopsis pyri*), an armored scale (*Parlatoria camelliae*), the tea parlatoria scale (*Parlatoria theae*), the black parlatoria scale (*Parlatoria ziziphi*), the fern scale (*Pinnaspis aspidistrae*), the camphor scale (*Pseudaonidia duplex*), the peony scale (*Pseudaonidia paeoniae*), the mulberry scale (*Pseudaulacaspis pentagona*), the white prunicola scale (*Pseudaulacaspis prunicola*), the arrowhead scale (*Unaspis yanonensis*);

the following from the order of the butterflies, moths and skippers (LEPIDOPTERA): swift moth (*Endoclita excrescens*), the grape treeborer (*Endoclita sinensis*), the moth (*Palpifer sexnotata*), the strawberry tortrix moth (*Acleris comariana*), the summer fruit tortrix moth (*Adoxophyes orana fasciata*), the smaller tea tortrix moth (*Adoxophyes* sp.), the Asiatic leafroller (*Archips breviplicanus*), the apple tortrix (*Archips fuscocupreanus*), the brown oak tortrix (*Archips xylosteanus*), the mat rush worm (*Bactra furfurana*), the tobacco leaf worm (*Cnephasia cinereipalpana*), the nut fruit tortrix (*Cydia kurokoi*), the greenish chestnut moth (*Eucoenogenes aestuosa*), the oriental fruit moth (*Grapholita molesta*), the oriental tea tortrix (*Homona magnanima*), the leafroller (*Choristoneura adumbratana*), the soybean pod borer (*Leguminivora glycinivorella*), the adzuki bean podworm (*Matsumuraeses azukivora*), the soybean pod worm (*Matsumuraeses falcana*), the soybean pod worm (*Matsumuraeses phaseoli*), the apple fruit licker (*Spilonota lechriaspis*), the eyespotted bud moth (*Spilonota ocellana*), the European grape berry moth (*Eupoecillia ambiguella*), the Chinese arrowed stemborer (*Gynnidomorpha mesotypa*), the yomogioo-hosohamaki (*Phtheochroides clandestina*), the mulberry bagworm (*Bambalina* sp.), the giant bagworm (*Eumeta japonica*), the tea bagworm (*Eumeta minuscule*), the European grain moth (*Nemapogon granellus*), the casemaking clothes moth (*Tinea translucens*), the pear leaf miner (*Bucculatrix pyrivorella*), the peach leafminer (*Lyonetia clerkella*), the apple leafminer (*Lyonetia prunifoliella*), the soybean leafroller (*Caloptilia soyella*), the tea leafroller (*Caloptilia theivora*), the ringo-hosoga (*Caloptilia zachrysa*), the persimmon leafminer (*Cuphodes diospyrosella*), the apple leafminer (*Phyllonorycter ringoniella*), the pear barkminer (*Spulerina astaurota*), the citrus leafminer (*Phyllocnistis citrella*), the grape leafminer (*Phyllocnistis toparcha*), the allium leafminer (*Acrolepiopsis sapporensis*), the yam leafminer (*Acrolepiopsis suzukiella*), the diamondback moth (*Plutella xylostella*), the apple fruit moth (*Argyresthia conjugella*), the vine tree borer (*Paranthrene regalis*), the cherry tree borer (*Synanthedon hector*), the persimmon fruit moth (*Stathmopoda masinissa*), the sweetpotato leaf folder (*Brachmia triannulella*), the peach fruit moth (*Carposina niponensis*), the pear leaf worm (*Illiberis pruni*), the Chinese cochlid (*Parasa sinica*), the oriental moth (*Monema flavescens*), the pear stinging caterpillar (*Narosoideus flavidorsalis*), the green cocklid (*Parasa consocia*), the persimmon cochlid (*Scopelodes contracus*), the rice stem borer (*Chilo suppressalis*), the rice leaffolder moth (*Cnaphalocrocis medinalis*), the yellow peach moth (*Conogethes punctiferalis*), the cotton caterpillar (*Diaphania indica*), the nashimadara-meiga (*Ectomyelois pyrivorella*), the Mediterranean flour moth (*Ephestia kuehniella*), the limabean pod borer (*Etiella zinckenella*), the persimmon bark borer (*Euzophera batangensis*), the mulberry pyralid (*Glyphodes pyloalis*), the cabbage webworm (*Hellulla undalis*), the rice leafroller (*Marasmia exigua*), the legume pod borer (*Maruca testulalis*), the cotton leafroller (*Notarcha derogate*), the Asian corn borer (*Ostrinia furnacalis*), the azuki bean borer (*Ostrinia scapulalis*), the butterbur borer (*Ostrinia zaguliaevi*), the bluegrass webworm (*Parapediasia teterrella*), the bean webworm (*Pleuroptya ruralis*), the yellow stem borer (*Scirpophaga incertulas*), the rice skipper (*Parnara guttata*), the red helen (*Papilio helenus*), the common yellow swallowtail (*Papilio machaon*), the swallowtail butterfly (*Papilio xuthus*), the eastern pale clouded yellow (*Colias erate poliographus*), the common cabbageworm (*Pieris rapae crucivora*), the long-tailed pea-blue (*Lampides boeticus*), the orange moth (*Angerona prunaria*), the Japanese giant looper (*Ascotis selenaria*), the phytomimetic giant geometer (*Biston robustum*), the plum cankerworm (*Cystidia couaggaria*), the pine caterpillar (*Dendrolimus spectabilis*), the tent caterpillar (*Malacosoma neustria testacea*), the apple caterpillar (*Odonestis pruni japonensis*), the coffee hawk moth (*Cephonodes hylas*), the grape horn worm (*Acosmeryx castanea*), the scarce chocolate-tip (*Clostera anachoreta*), the poplar prominent (*Clostera anastomosis*), the Japanese buff-tip moth (*Phalera flavescens*), the oak caterpillar (*Phalerodonta manleyi*), the lobster moth (*Stauropus fagi persimilis*), the tea tussock moth (*Euproctis pseudoconspersa*), the brown-tail moth (*Sphrageidus similis*), the oriental tussock moth (*Artaxa subflava*), the gypsy moth (*Lymantria dispar*), the white-spotted tussock moth (*Orgyia thyellina*), the Fall webworm moth (*Hyphantria cunea*), the mulberry tiger moth (*Spilosoma imparilis*), the three-spotted plusia (*Acanthoplusia agnata*), the eastern alchymist (*Aedia leucomelas*), the black cutworm (*Agrotis ipsilon*), the turnip moth (*Agrotis segetum*), the hibiscus looper (*Anomis mesogona*), the beet semi-looper (*Autographa nigrisigna*), the cabbage looper (*Trichoplusia ni*), the cotton bollworm (*Helicoverpa armigera*), the cape gooseberry budworm (*Helicoverpa assulta*), the flax budworm (*Heliothis maritime*), the cabbage Moth (*Mamestra brassicae*), the rice green caterpillar (*Naranga aenescens*), the oriental armyworm (*Pseudaletia separata*), the pink stem borer (*Sesamia inferens*), the lawn grass cutworm (*Spodoptera depravata*), the beet armyworm (*Spodoptera exigua*), the common cutworm (*Spodoptera litura*), the apple dagger moth (*Trianea intermedia*), the sorrel cutworm (*Viminia rumicis*), the cutworm (*Xestia c-nigrum*);

the following of the beetle order (COLEOPTERA): brown chafer (*Adoretus tenuimaculatus*), the cupreous chafer (*Anomala cuprea*), the soybean beetle (*Anomala rufocuprea*), the flower beetle (*Eucetonia pilifera*), the aohanamuguri (*Cetonia roelofsi*), the yellowish elongate chafer (*Heptophylla picea*), the Japanese cockchafer (*Melolontha japonica*), the scarab beetle (*Mimela splendens*), the citrus flower chafer (*Oxycetonia jucunda*), the Japanese beetle (*Popillia japonica*), the varied carpet beetle (*Anthrenus verbasci*), the black carpet beetle (*Attagenus unicolor japonicus*), the cigarette beetle (*Lasioderma serricorne*), the powderpost beetle (*Lyctus brunneus*), the corn sap beetle (*Carpophilus dimidiatus*), the dried fruit beetle (*Carpophilus hemipterus*), the leaf feeding ladybird (*Epilachna vigintioctomaculata*), the phytophagous ladybird beetle (*Epilachna vigintioctopunctata*), the black fungus beetle (*Alphitobius laevigatus*), the yellow-dappled longicorn (*Neatus picipes*), the smalleyed flour beetle (*Palorus ratzeburgii*), the depressed flour beetle (*Palorus subdepressus*), the yellow mealworm (*Tenebrio molitor*), the red flour beetle (*Tribolium castaneum*), the confused flour beetle (*Tribolium confusum*), the bean blister beetle (*Epicauta gorhami*), the kimadara-kamikiri (*Aeolesthes chrysothrix*), the white spotted longicorn beetle (*Anoplophora malasiaca*), the Japanese pine sawyer (*Monochamus alternatus*), the yellow-spotted longicorn beetle (*Psacothea hilaris*), the grape borer (*Xylotrechus pyrrhoderus*), the monkeypod round-headed borer (*Xystrocera globosa*), the azuki bean weevil (*Callosobruchus chinensis*), the cucurbit leaf beetle (*Aulacophora femoralis*), the chairosaru-hamushi (*Basilepta balyi*), the tortoise beetle (*Cassida nebulosa*), the tensaitobi-hamushi (*Chaetocnema concinna*), the sweetpotato leaf beetle (*Colasposoma dauricum*), the juushihoshiku-binaga-hamushi (*Crioceris quatuordecimpunctata*), the rice rootworm (*Donacia provosti*), the ruri-hamushi (*Linaeidea aenea*), the soybean flea beetle (*Luperomorpha tenebrosa*), the two-striped leaf beetle (*Medythia nigrobilineata*), the rice leaf beetle (*Oulema oryzae*), the tropical legume leaf beetle (*Pagria signata*), the daikon leaf beetle (*Phaedon brassicae*), the striped flea beetle (*Phyllotreta striolata*), the umechok-kiri-zoumushi (*Involvulus cupreus*), the peach curculio (*Rhynchites heros*), the sweet potato weevils (*Cylas formicarius*), the apple blossom weevil (*Anthonomus pomorum*), the daikonsaru-zoumushi (*Ceutorhynchus albosuturalis*), the chestnut weevil (*Curculio sikkimensis*), the rice plant weevil (*Echinocnemus squameus*), the West Indian sweetpotato weevil (*Euscepes postfasciatus*), the lesser clover-leaf weevil (*Hypera nigrirostris*), the alfalfa weevil (*Hypera postica*), the rice water weevil (*Lissorhoptrus oryzophilus*), the vegetable weevil (*Listroderes costirostris*), the leaf weevil (*Phyllobius armatus*), the chibikofuki-zoumushi (*Sitona japonicus*), the rice weevil (*Sitophilus oryzae*), the maize weevil (*Sitophilus zeamais*), the hunting billbug (*Sphenophrus venatus vestitus*);

the following from the sawfly, wasp, bee, and ant order (HYMENOPTERA): the cabbage sawfly (*Athalia japonica*), the turnip sawfly (*Athalia rosae ruficornis*), the apple argid sawfly (*Arge mali*), the large rose sawfly (*Arge pagana*) and the oriental chestnut gall wasp (*Dryocosmus kuriphilus*);

the following from the fly order (DIPTERA): the rice crane fly (*Tipula aino*), the sciarid fly (*Bradysia agrestis*), the soybean pod gall midge (*Asphondylia* sp.), the melon fly (*Dacus cucurbitae*), the oriental fruit fly (*Dacus dorsalis*), the citrus fruit fly (*Dacus tsuneonis*), the Japanese cherry fruit fly (*Rhacochlaena japonica*), the rice leaf miner (*Hydrellia griseola*), the rice whorl maggot (*Hydrellia sasakii*), the cherry drosophila (*Drosophila suzukii*), the rice stem maggot (*Chlorops oryzae*), the wheat stem maggot (*Meromyza nigriventris*), the Japanese rice leaf miner (*Agromyza oryzae*), the pea leaf miner (*Chromatomyia horticola*), the celery miner fly (*Liriomyza bryoniae*), the stone leek leafminer (*Liriomyza chinensis*), the American serpentine leafminer (*Liriomyza trifolii*), the vegetable leafminer (*Liriomyza sativae*), the pea leafminer (*Liriomyza huidobrensis*), the onion fly (*Delia antiqua*), the bean seed fly (*Delia platura*), the beet leaf miner (*Pegomya cunicularia*), the house fly (*Musca domestica*), the blowfly (*Phormia regina*), the house-gnat (*Culex pipiens pallens* Coquillett), the chikaieka (*Culex pipiens molestus* Forskal), the shina-hamadaraka (*Anopheles (Anopheles) sinensis* Wiedemann), and the Asian tiger mosquito (*Aedes albopictus* (Skuse)).

In addition, examples that may be given of stored grain insects that may be controlled by the invention include, the but are not limited to, the following: the redlegged ham beetle (*Necrobia rufipes*), the soybean beetle (*Callosobruchus analis*), the redshouldered ham beetle (*Necrobia ruficollis*), the Pineapple beetle (*Urophorus humeralis*), the American spider beetle (*Mezium americanum*), the stored nut moth (*Paralipsa gularis*), the bean weevil (*Acanthoscelides obtectus*), the pea weevil (*Bruchus pisorum*), the Australian spider beetle (*Ptinus tectus*), the larger grain borer (*Prostephanus truncatus*), the broad-horned flour beetle (*Gnathocerus cornutus*), the merchant grain beetle (*Oryzaephilus mercator*), the meal moth (*Pyralis farinalis*), the Kashmir flour beetle (*Tribolium freemani*), the foreign grain beetle (*Ahasverus advena*), the lesser meal worm (*Alphitobius diaperinus*), the rice moth (*Corcyra cephalonica*), the golden spider beetle (*Niptus holoeucus*), the granary weevil (*Sitophilus granaries*), the black flour beetle (*Tribolium madens*), the destructive flour beetle (*Tribolium destructor*), the Nemapogon (*Nemapogon granella*), the maize weevil (*Sitophilus zeamais*), the broadnosed grain weevil (*Caulophilus oryzae*), the cadelle beetle (*Tenebroides mauritanicus*), the grain worm (*Martyringa xeraula*), the longheaded flour beetle (*Latheticus oryzae*), the slenderhorned flour beetle (*Gnathocerus maxillosus*), the lesser grain borer (*Rhizopertha dominica*), the mould beetle (*Aridius nodifer*), the sap beetle (*Carpophilus pilosellus*), the dark mealworm (*Tenebrio obscurus*), the black rice worm (*Aglossa dimidiata*), the rusty grain beetle (*Cryptolestes ferrugineus*), the drugstore beetle (*Stegobium paniceum*), the almond moth (*Ephestia cautella*), the broad bean weevil (*Bruchus rufimanus*), the square-necked grain beetle (*Cathartus quadricollis*), the hairy fungus beetle (*Typhaea stercorea*), the tsuyahimemakimusshi (*Holoparamecus signatus*), the seed beetle (*Pagiocerus frontalis*), the niseduriyakesikisui (*Carpophilus delkeskampi*), the spider beetle (*Gibbium aequinoctiale*), the sawtoothed grain beetle (*Oryzaephilus surinamensis*), the Indian-meal moth (*Plodia interpunctella*), the hide beetle (*Dermestes maculates*), the cowpea weevil (*Callosobruchus phaseori*), the rusty grain beetle (*Cryptolestes pusilloides*), the angoumois grain moth (*Sitotroga cerealella*), the khapra beetle (*Trogoderma granarium*), the brown spider beetle (*Ptinus clavipes*), the larger cabinet beetle (*Trogoderma inclusum*), the lentil pest (*Bruchus lentis*), a the futagomamezoumushi (*Callosobruchus subinnotatus*), the Mexican bean weevil (*Zabrotes subfasciatus*), the vetch bruchid (*Bruchus brachialis*), the Siamese grain beetle (*Lophocaterus pusillus*), the munabirohimehamakimushi (*Dienerella costulata*), the Mexican grain beetle (*Pharaxonotha kirschii*), the peanut bruchid (*Caryedon serratus*), the cowpea bruchid (*Callosobruchus maculatus*), the checkered beetle (*Necrobia violacea*), the rhodesian bean weevil (*Callosobruchus rhodesianus*) and the coffee bean weevil (*Araecerus fasciculatus*).

Examples that may be given of timber pest insects that may be controlled by the invention include, but are not limited to the following: the niisima-kikuimushi (*Sueus niisimai*), the coffee-kikuimushi (*Taphrorychus coffeae*), the sazankakoatomaru-kikuimushi (*Poecilips oblongus*), the black twig borer (*Xylosandrus compactus*), the mulberry bark beetle (*Xyleborus atratus*), the futairo-kikuimushi (*Xyleborus bicolor*), the akagashinoki-kikuimushi (*Xyleborus cincisus*), redbay ambrosia beetle (*Xyleborus glabratus*), the ainokikuimushi (*Xyleborus interjectus*), camphor shot borer (*Xylosandrus mutilatus*) and the todomatsuoo-kikuimushi (*Xyleborus validus*).

The following may be given as examples of the fungicidal compound included in the pest control composition of the invention, but it should be noted that the invention is not limited thereto.

The examples include: carboxamide fungicides, such as thifluzamide, flutolanil, mepronil, pencycuron, ethaboxam, oxycarboxin, carboxin, and silthiofam;

melanin biosynthesis inhibitor fungicides, such as carpropamid, diclocymet, tricyclazole, pyroquilon, fenoxanil, and fthalide;

strobilurin fungicides, such as azoxystrobin, metominostrobin, orysastrobin, kresoxim-methyl, fluoxastrobin, trifloxystrobin, dimoxystrobin, pyraclostrobin, and picoxystrobin;

antibiotics, such as kasugamycin, validamycin, benzylaminobenzenesulfonic acid salt of blasticidin-S, tecloftalam, oxytetracycline, streptomycin, blasticidin-S, mildiomycin, and polyoxins;

pyrimidine fungicides, such as ferimzone, fenarimol, pyrifenox, nuarimol, and bupirimate;

azole fungicides, such as simeconazole, furametpyr, ipconazole, triflumizole, prochloraz, pefurazoate, imazalil, imibenconazole, etridiazole, epoxiconazole, fumaric acid salt of oxpoconazole, diniconazole, difenoconazole, cyproconazole, tetraconazole, tebuconazole, triadimenol, triadimefon, triticonazole, bitertanol, fenbuconazole, fluquinconazole, flusilazole, flutriafol, prothioconazole, propiconazole, bromuconazole, hexaconazole, penconazole, metconazole, and fluquinconazole;

copper fungicides, such as copper, copper nonylphenolsulfonate, basic copper oxychloride, basic copper sulphate, oxine copper, DBEDC, anhydrous copper sulfate, and copper II hydroxide;

benzimidazole fungicides, such as thiophanate-methyl, benomyl, thiabendazole, thiophanate, carbendazim, and fuberidazole;

organophosphorus fungicides, such as EDDP, IBP, tolclofos-methyl, fosetyl, dinocap, and pyrazophos;

acylalanine fungicides, such as metalaxyl, oxadixyl, benalaxyl, and metalaxyl-M;

dicarboximide fungicides, such as iprodione, procymidone, vinclozolin, and chlozolinate;

dithiocarbamate fungicides, such as thiuram, mancozeb, propineb, zineb, metiram, maneb, ziram, and amobam;

soil disinfectants, such as hydroxyisoxazol (hymexazol), methasulfocarb, chloropicrin, flusulfamide, dazomet, methylisothiocyanate, potassium salt of hydroxyisoxazol, etridiazole, 1,3-dichloropropene, and carbam;

organochlorine fungicides, such as TPN and captan;

anilino pyrimidine fungicides, such as mepanipyrim, cyprodinil, and pyrimethanil;

natural products, such as rapeseed oil and machine oil;

inorganic fungicides, such as sulfur, lime sulfur mixture, zinc sulfate, fentin, sodium hydrogencarbonate, potassium hydrogencarbonate, and hypochlorite;

morpholine fungicides, such as dimethomorph, fenpropidin, fenpropimorph, spiroxamine, tridemorph, dodemorph, and flumorph;

fungicides, such as iprovalicarb, imazalil-S, iminoctadine albesilate, quinoxyfen, chinomethionat, metallic silver, chlorothalonil, chloroneb, cyazofamid, diethofencarb, dichlofluanid, dichloram, dithianon, diflumetorim, dimethirimol, cymoxanil, silthiofam, spiroxamine, zoxamide, thiadiazine (minleb), dodine, triforine, tolylfluanid, nitrothal-isopropyl, famoxadone, fenamidone, fenitropan, fenpiclonil, fenhexamid, folpet, fluazinam, fluopicolide, fluoroimide, propamocarb, propamocarb hydrochloride, propylene glycol fatty acid esters, calcium salt of prohexadione, benthiazole, benthiavalicarb-isopropyl, myclobutanil, organic nickel, resveratrol, diclomezine, iminoctadine acetate, isoprothiolane, tiadinil, probenazole, acibenzolar-S-methyl, fludioxonil, fosetyl-aluminum, guazatine and triazoxide.

In the invention, a plant seed refers to something that stores nutrients for seedlings to sprout and is used for propagation in agriculture. Specific examples that may be given include, but are not limited to: seeds, such as of corn, *Coix* lacryma-joli (Job's Tears), Japanese millet, buckwheat, soya bean, azuki bean, common bean, pea, broad bean, peanut, hyacinth bean, cabbage, Brussels sprout, Japanese radish, non head-forming *brassica* leaf vegetables, cotton, rice, sugar beet, table beet, wheat, barley, sunflower, tomato, cherry tomato, chilli peppers, cucumber, watermelon, bitter melon, melon, oriental pickling melon, winter melon, eggplant, spinach, podded pea, green bean, immature broad bean, green pea, asparagus, okra, garland chrysanthemum, carrot, parsley, Welsh onion, scallion, lettuce, non head-forming lettuces, Japanese pumpkin, sugarcane, tobacco, sweet pepper, rape, rye, and oats; seed tubers, such as taro, potato, sweet potato, yam and konnyaku; bulbs, such as edible lily, tulip, narcissus, hyacinth, amaryllis, lily, gladiolus and crocus; and seed bulbs, such as shallot, ginger, garlic and lotus root. Moreover, the pest insect damage control by application to these plant seeds and plant bodies is not only related to these seeds, seed tubers, and seed bulbs themselves, but also to the products such as stems, leaves, fruits and the like that grow therefrom.

The plant seeds and plant bodies in this specification may also be plant seeds, cereals, legumes, vegetables, and flowering plants which have undergone genetic transformation, in other words, plants that do not initially exist in nature but are produced by manipulating genes and the like artificially. Examples thereof include, but are not limited to: plants imparted with herbicide resistance such as soya bean, corn, and cotton; cold adapted plants such as rice and tobacco; and plants imparted with the functionality of producing insecticidal substance, such as corn, cotton, and potato.

Stored cereals, stored legumes, stored fruits, and stored vegetables refer to cereals, legumes, fruits, vegetables, and the like which are stored and saved for domestic distribution or export/import, and these are generally provided for consumption or processing. Examples that may be given thereof include, rice, barley, wheat, corn, rye, oat, pea, kidney bean, black-eyed bean, saltani bean, saltapia bean, butter bean, pegia bean, white bean, lima bean, broad bean, soya bean, azuki bean, apricot, Japanese plum, cherry, plum, nectarine, peach, orange, grapefruit, Chinese citron, lime, lemon, loquat, quince, apple, avocado, kiwi fruit, guava, date, pineapple, passion fruit, banana, papaya, mango, strawberry, cranberry, huckleberry, blackberry, blueberry, persimmon, watermelon, grape, oriental melon, melon, turnip, cauliflower, cabbage, watercress, kale, horseradish, radish, broccoli, sweet potato, konnyaku tubers, taro, potato, Japanese pumpkin, cucumber, oriental pickling melon, artichoke, endive, burdock, salsify, chicory, lettuce, shiitake mushroom, mushroom, celery, carrot, parsnip, parsley, tomato, sweet pepper, asparagus, onion, garlic, Welsh onion, scallion, green soya bean, okra, sugar cane, ginger, sugar beet, spinach, immature kidney beans, immature peas, oilseeds (such as sesame seeds, sunflower seeds, oilseed rape, safflower seeds, and cotton seeds), nuts (such as almond, ginkgo nut, chestnut, walnut, and pecan), cacao bean, coffee bean, tea, and hops.

Silage refers to feed and the like that is stored and saved for domestic distribution or export/import, and is generally provided for the breeding of livestock and the like. Specific examples that may be given thereof include cereals, legumes, and the like.

Stored flowering plants refers to potted plants, flower arrangements, cut flowers, bulbs, seeds, and the like stocked for domestic distribution or export/import, and are mainly provided for decoration and cultivation. Examples that may be given thereof include, orchid, Rumohra, chrysanthemum, xerophyllum, Eurya japonica, lily, freesia, wild pink, rose, anthurium, carnation, tulip and the like.

Export/import timber refers to logs or sawn timbers that are stored/stockpiled for the purpose of export/import, and is generally provided for processing, construction, and the like. Examples that may be given thereof include hemlock, Douglas fir, spruce, *Picea* jezoensis, Abies sachalinensis, larch, lauan, and the like.

The content of the dinotefuran as an active ingredient of the composition of the invention is normally in the range of 0.005% to 99% with respect to the total weight of the composition, preferably is 0.01% to 90%, and is still more preferably 0.1% to 85%. On the other hand, the content of the fungicidal compound is normally in the range of 0.005% to 99% with respect to the total weight of the composition, preferably is 0.01% to 90%, and still more preferably is 0.1% to 85%. The total content of dinotefuran together with other fungicidal compound(s) is normally in the range of 0.005% to 99% with respect to the total weight of the composition, preferably is 0.01% to 90%, and is still more preferably 0.1% to 85%.

A carrier used for the above formulation is not particularly limited, and if it is a carrier that is usually used for agricultural formulation, then either a solid or a liquid carrier may be used. As a solid carrier, the following may be given as examples: inorganic substances, such as bentonite, montmorillonite, kaolinite, diatomaceous earth, white clay, talc, clay, vermiculite, gypsum, calcium carbonate, amorphous silica, ammonium sulfate; vegetable organic substance, such as soya bean flour, wood flour, saw dust, wheat flour, lactose, sucrose, and glucose; and urea and the like. As a liquid carrier, the following may be given as examples: aromatic hydrocarbons such as toluene, xylene, and cumene, and naphthenes; paraffin hydrocarbons, such as n-paraffin, iso-paraffin, liquid paraffin, kerosene, mineral oil, and polybutene; ketones, such as acetone, and methyl ethyl ketone; ethers, such as dioxane and diethylene glycol dimethyl ether; alcohols, such as ethanol, propanol, and ethylene glycol; carbonates, such as ethylene carbonate, propylene carbonate, and butylene carbonate; aprotic solvents such as dimethylformamide, and dimethyl sulfoxide; and water, and the like.

Furthermore, in order to reinforce the effect of the invention compound the following adjuvants (binders, disintegrators, pH adjusters, antifoams and antifreezing agents) may also be used, alone or in combinations thereof, according to the purpose and in consideration of the form of the formulation, the treatment method and the like. As adjuvants, surfactants may be used that are usually used in agricultural formulation for purposes such as emulsification, dispersion, spreading, and wetting, and examples that may be given of such surfactants include, but are not limited to: nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene castor oils, polyoxyethylene alkyl ethers, polyoxyethylene alkyl phenyl ethers, polyoxyethylene dialkyl phenyl ethers, formaldehyde condensates of polyoxyethylene alkyl phenyl ether, polyoxyethylene-polyoxypropylene block polymer, alkyl polyoxyethylene-polyoxypropylene block polymer ether, alkylphenyl polyoxyethylene-polyoxypropylene block polymer ether, polyoxyethylene alkylamine, polyoxyethylene fatty acid amide, polyoxyethylene bisphenyl ether, polyoxyalkylene benzylphenyl ether, polyoxyalkylene styryl phenyl ether, polyoxyalkylene adducts of a higher alcohol, polyoxyethylene ethers, ester modified silicones, and fluorosurfactants; anionic surfactants such as alkyl sulfates, polyoxyethylene diallyl ether sulfates, polyoxyethylene alkyl ether sulfates, polyoxyethylene alkylphenyl ether sulfates, polyoxyethylene benzylphenyl ether sulfates, polyoxyethylene styryl phenyl ether sulfates, polyoxyethylene-polyoxypropylene block polymer sulfates, paraffin sulfonates, alkane sulfonates, AOS, dialkyl sulfosuccinate, alkylbenzene sulfonates, naphthalene sulfonates, dialkyl naphthalene sulfonates, formaldehyde condensates of naphthalene sulfonates, alkyl diphenyl ether disulfonates, lignin sulfonates, polyoxyethylene alkyl phenyl ether sulfonates, polyoxyethylene alkyl ether sulfosuccinate half esters, fatty acid salts, N-methyl fatty acid sarcosinate, resinates, polyoxyethylene alkyl ether phosphates, polyoxyethylene phenyl ether phosphates, polyoxyethylene dialkyl phenyl ether phosphates, polyoxyethylene benzylated phenyl ether phosphates, polyoxyethylene benzylated phenylphenyl ether phosphates, polyoxyethylene styrylated phenyl ether phosphates, polyoxyethylene benzylated phenylphenyl ether phosphates, polyoxyethylene-polyoxypropylene block polymer phosphates, polyoxyethylene diallyl ether sulfates, phosphatidylcholine, phosphatidyl ethanolimine, alkyl phosphates and sodium tripolyphosphates; polyanion type high molecular surfactant derived from acrylic acid with acrylonitrile, acrylamide-methylpropanesulfonic acid; cationic surfactants, such as alkyl trimethyl ammonium chloride, methyl polyoxyethylene alkyl ammonium chloride, alkyl N-methylpyridinium bromide, mono-methylated ammonium chloride, dialkyl methalated ammonium chloride, alkyl pentamethyl propylene amine dichloride, alkyl dimethyl benzalkonium chloride, and benzethonium chloride; and amphoteric surfactants, such as dialkyl diaminoethyl betaines and alkyl dimethyl benzyl betaine.

As a binder, examples that may be given include sodium arginate, polyvinyl alcohols, gum arabic, sodium CMC, bentonite, and the like.

Examples that may be given of disintegrants include sodium CMC, crosscarmellose sodium, and examples of stabilizers include hindered phenol based antioxidants, benzotriazol based and hindered amine based ultraviolet absorbers, and the like.

Phosphoric acid, acetic acid, and sodium hydroxide may be used as a pH adjuster, and industrial fungicides and antifungal agents, such as 1,2-benzisothiazolin-3-one and the like, may be added for prevention of bacteria and molds.

As a thickener, xanthane gum, guar gum, sodium CMC, gum arabic, polyvinyl alcohols, montmorillonite, and the like may also be used.

As required, silicone compounds may be used as antifoaming agents and propylene glycol, ethylene glycol, and the like may be used as antifreezing agents.

When applying the composition of the invention to plant seeds, plant seeds may be immersed in a composition as it is. Alternatively, the composition may be diluted to a suitable concentration with a suitable carrier, and then used by immersion, dust coating, spraying, coating treatment, or the like, to plant seeds.

There are no particular limitations to suitable carriers, and examples that may be given thereof include: liquid carriers, such as water or organic solvents such as ethanol; solid carriers, such as inorganic substances like bentonite, montmorillonite, kaolinite, diatomaceous earth, white clay, talc, clay, vermiculite, gypsum, calcium carbonate, amorphous silica, and ammonium sulfate; vegetable organic substances, such as soya bean flour, wood flour, saw dust, wheat flour, lactose, sucrose, and glucose; and urea.

The dilution rate of formulation may be set appropriately, and the dilution rate is suitably chosen according to the candidate crop for application, type of disease damage, and type of insect damage, and the dilution rate is suitably 1 to 50,000 times, is preferably 1 to 20,000 times, and is still more preferably 1 to 10,000 times.

For carrying out dust coating, spraying, and coating treatment, a suitable amount of the formulation used is usually about 0.05% to 50% of dry plant seed weight, more preferably 0.1% to 40%, and still more preferably 0.1% to 30%. However, the amount used is not limited to these ranges, and may be varied according to the form of the formulation and to the kind of plant seed used as the candidate for treatment.

EXAMPLES

The invention will now be explained in detail, with reference to Examples and Test Examples.

Example 1

Powder Formulation 1 part of dinotefuran, 10 parts of hymexazol, 88.5 parts of clay, and 0.5 parts of DRILESS B (trade name, an aggregating agent from Sankyo Co., Ltd.) were uniformly mixed together and ground, and a powder formulation containing dinotefuran at 1% and hymexazol at 10% was obtained.

Example 2

Wettable Powder 40 parts of dinotefuran, 4 parts of flusulfamide, 1 part of sodium ligninsulfonate, 5 parts of white carbon, and 50 parts of diatomaceous earth were mixed together and ground, and a wettable powder containing dinotefuran at 40% and flusulfamide at 4% was obtained.

Example 3

Wettable Powder 70 parts of dinotefuran, 4 parts of flusulfamide, 1 part of sodium ligninsulfonate, 5 parts of white carbon, and 20 parts of diatomaceous earth were mixed together and ground, and a wettable powder containing dinotefuran at 70% and flusulfamide at 4% was obtained.

Example 4

Wettable Powder 70 parts of dinotefuran, 4 parts of hymexazol, 1 part of sodium ligninsulfonate, 5 parts of white carbon, and 20 parts of diatomaceous earth were mixed together and ground, and a wettable powder containing dinotefuran at 70% and hymexazol at 4% was obtained.

Example 5

Wettable Powder 70 parts of dinotefuran, 4 parts of flusulfamide, 4 parts of hymexazol, 1 part of sodium ligninsulfonate, 5 parts of white carbon, and 16 parts of diatomaceous earth were mixed together and ground, and a wettable powder containing dinotefuran at 70%, flusulfamide at 4% and hymexazol at 4% was obtained.

Reference Example 1

Wettable Powder 70 parts of dinotefuran, 1 part of sodium ligninsulfonate, 5 parts of white carbon, and 24 parts of diatomaceous earth were mixed together and ground, and a wettable powder containing dinotefuran at 70% was obtained.

Reference Example 2

Wettable Powder 4 parts of flusulfamide, 1 part of sodium ligninsulfonate, 5 parts of white carbon, and 90 parts of diatomaceous earth were mixed together and ground, and a wettable powder containing flusulfamide at 4% was obtained.

Reference Example 3

Wettable Powder 4 parts of hymexazol, 1 part of sodium ligninsulfonate, 5 parts of white carbon, and 90 parts of diatomaceous earth were mixed together and ground, and a wettable powder containing hymexazol at 4% was obtained.

Reference Example 4

Wettable Powder 4 parts of flusulfamide, 4 parts of hymexazol, 1 part of sodium ligninsulfonate, 5 parts of white carbon, and 88 parts of diatomaceous earth were mixed together and ground, and a wettable powder containing flusulfamide at 4% and hymexazol at 4% was obtained.

Example 6

Emulsion 15 parts of dinotefuran, 15 parts of triflumizole, 10 parts of cyclohexane, 40 parts of xylene, and 20 parts of SORPOL (trade name, a surfactant made by Toho Chemical Industries Co., Ltd.) were uniformly dissolved and mixed, and an emulsion containing dinotefuran at 15% and triflumizole at 15% was obtained.

Example 7

Granular Wettable Powder 20 parts of dinotefuran, 50 parts of benomyl, 3 parts of sodium CMC, 5 parts of sodium alkyl sulfate, and 22 parts of clay were uniformly mixed, and then kneading with water, pelletization, drying, and particle size regulation were performed thereto, and a granular wettable powder containing dinotefuran at 20% and benomyl at 50% was obtained.

Example 8

Flowable

Wet grinding was performed using a sand grinder on 20 parts of dinotefuran, 4 parts of flusulfamide, 5 parts of propylene glycol, 5 parts of polyoxyethylene oleate, 5 parts of polyoxyethylene diallyl ether sulfate, 0.2 parts of silicone antifoaming agent, and 60.8 parts of water, and a flowable containing dinotefuran at 20% and flusulfamide at 4% was obtained.

Example 9

Flowable

Wet grinding was performed using a sand grinder on 20 parts of dinotefuran, 4 parts of hymexazol, 5 parts of propylene glycol, 5 parts of polyoxyethylene oleate, 5 parts of polyoxyethylene diallyl ether sulfate, 0.2 parts of silicone antifoaming agent, and 60.8 parts of water, and a flowable containing dinotefuran at 20% and hymexazol at 4% was obtained.

Reference Example 5

Flowable

Wet grinding was performed using a sand grinder on 20 parts of dinotefuran, 5 parts of propylene glycol, 5 parts of polyoxyethylene oleate, 5 parts of polyoxyethylene diallyl ether sulfate, 0.2 parts of silicone antifoaming agent, and 64.8 parts of water, and a flowable containing dinotefuran at 20% was obtained.

Reference Example 6

Flowable

Wet grinding was performed using a sand grinder on 4 parts of flusulfamide, 5 parts of propylene glycol, 5 parts of polyoxyethylene oleate, 5 parts of polyoxyethylene diallyl ether sulfate, 0.2 parts of silicone antifoaming agent, and 80.8 parts of water, and a flowable containing flusulfamide at 4% was obtained.

Reference Example 7

Flowable

Wet grinding was performed using a sand grinder on 4 parts of hymexazol, 5 parts of propylene glycol, 5 parts of polyoxyethylene oleate, 5 parts of polyoxyethylene diallyl ether sulfate, 0.2 parts of silicone antifoaming agent, and 80.8 parts of water, and a flowable containing hymexazol at 4% was obtained.

Test Example 1

Control Effect Against Sugar Beet Seedling Damping Off

A *Rhizoctonia* culture and a *Pythium* culture were separately cultivated at 25° C. for seven days in a wheat bran medium, and after respectively grinding, the *Rhizoctonia* culture and/or the *Pythium* culture were added to and mixed in with sterilized soil, and the mixtures were filled in plastic pots to obtain infected soils each containing:

*Rhizoctonia* culture at 0.1% with respect to the sterilized soil;

*Pythium* culture at 0.1% with respect to the sterilized soil, and

*Rhizoctonia* culture at 0.1% and *Pythium* culture at 0.1%, with respect to the sterilized soil.

Subsequently, amounts of 3.5% and 7% per kg of seed of the powder of Example 1 containing active ingredients of dinotefuran and hymexazol, and amounts of 0.5% and 1.0% per kg of seed of a commercially available seed fungicide (TACHIGAREN, a dust coating agent containing hymexazol made by Sankyo Agro Co., Ltd.) were added to sugar beet seed (variety: ABEND), and well mixed. The sugar beet seeds to which chemical treatment had been carried out were sown at five seeds per pot, with a total of 20 pots, and these pots were grown on in a greenhouse. The number of non-sprouting seeds was examined at 7 days after sowing, and the seedling dieback number was examined at 14 days after sowing, with the naked eye, and the seedling dieback rate was computed by the following Formula 1. Moreover, the existence or not of occurrences of phytotoxicity was also examined with the naked eye. Results are shown in Table 1.

Seedling dieback rate=((number of non-sprouting seeds+seedling dieback number)/number of seeds sown)×100     Formula 1

TABLE 1

| Test compound | Active ingredient amount (g/kg seed) | Seedling dieback rate with Rhizoctonia (%) | Seedling dieback rate with Pythium (%) | Seedling dieback rate with Rhizoctonia and Pythium (%) | Phytotoxicity |
|---|---|---|---|---|---|
| Powder formulation of the invention (Example 1) | Dinotefuran 0.7 + Hymexazol 7.0 | 50.6 | 0.9 | 42.2 | None |
|  | Dinotefuran 0.35 + Hymexazol 3.5 | 53.6 | 4.1 | 48.8 | None |
| Control seed disinfectant TACHIGAREN powder formulation | 7.0 | 65.8 | 1.1 | 59.1 | None |
|  | 3.5 | 63.9 | 4.3 | 58.6 | None |
| No treatment | — | 65.3 | 50.4 | 57.5 |  |

Test Example 2

Control Effect Against Common Scab and Black Scarf in Potato

A *Rhizoctonia* culture was cultivated in a concrete pot in a wheat bran medium at 25° C. for seven days, and this was then added at 0.1% by weight with respect to steam sterilized soil and mixed in uniformly. A *Rhizoctonia* culture cultivated by the same method was added at 0.1% with respect to soil extracted from a common scab infected field and mixed in uniformly, and soil was also extracted from a common scab infected field. These three soil compositions were placed, respectively, into concrete pots (50 cm length×50 cm width× 30 cm depth) and the test soils were thereby obtained.

Next, after carrying out dip treatment of the seed tubers of potato (variety: Baron) into, respectively, 50 times diluents of the wettable powder produced in Example 2 and in Reference Example 2 (comparative agents), and of a commercial fungicide (NOTTOBAN, a wettable powder containing tolclofos-methyl and flusulfamide, made by Sumitomo Chemical Co., Ltd.), the seed tubers were air dried and then two seed tubers were buried per pot. For the non-treated category, seed tubers that had not undergone chemical treatment were buried. 110 days after burying the seed tubers, the newly formed potatoes were dug up, and the existence of disease onset was examined with the naked eye, and the disease onset potato ratio was computed by the following Formula 2. Five replicates of the above test were performed, and the average values of the results are shown in Table 2.

Disease onset potato ratio=(number of potatoes with disease onset/total number of potatoes examined)×100   Formula 2

Test Example 3

Control Effect Against Bakanae Disease

Rice seeds (variety: Tanginbozu-dwarf) infected with benomyl-resistant Bakanae disease was mixed respectively with the emulsion produced in Example 6 containing dinotefuran and triflumizole as active ingredients, and mixed with a commercially available seed disinfectant (TRIFMIN, trade name, a wettable powder containing triflumizole made by Nippon Soda Co., Ltd.) as a control chemical, and a dressing treatment was carried out. After soaking the seeds (at 15° C. for three days) and forced sprouting (at 28° C. for one day), the seeds to which chemical treatment had been carried out were each sown at 100 seeds per plastic pot, and grown on in a greenhouse. The existence of disease onset was examined for all the seedlings with the naked eye at 20 days after sowing, and the disease onset seedling ratio was computed by the following Formula 3. Moreover, the existence or not of occurrences of phytotoxicity was also examined with the naked eye. Three replicates of the above test were performed, and the average values of the results are shown in Table 3.

Disease onset seedling ratio=(number of diseased seedlings/number of seeds sown)×100   Formula 3

TABLE 3

| Test compound | Active ingredient amount (g/kg seed) | Disease onset seedling ratio (%) | Phytotoxicity |
|---|---|---|---|
| Emulsion of the invention (Example 6) | Dinotefuran 5.0 + Triflumizole 5.0 | 32.4 | None |

TABLE 2

| Test compound | Dilution rate | Disease onset potato ratio in soil infected with black scarf (%) | Disease onset potato ratio in soil infected with common scab (%) | Disease onset potato ratio in soil infected with black scarf and common scab (%) | Phytotoxicity |
|---|---|---|---|---|---|
| Wettable powder of the invention (Example 2) | 50 times | 20.5 | 18.6 | 18.4 | None |
| Comparative wettable powder (Reference Example 2) | 50 times | 28.2 | 25.3 | 26.2 | None |
| Control chemical NOTTOBAN wettable powder | 50 times | 1.3 | 27.2 | 28.3 | None |
| No treatment |  | 25.2 | 50.5 | 63.1 |  |

TABLE 3-continued

| Test compound | Active ingredient amount (g/kg seed) | Disease onset seedling ratio (%) | Phytotoxicity |
|---|---|---|---|
| Control seed disinfectant TRIFMIN emulsion | Triflumizole 5.0 | 41.5 | None |
| No treatment | — | 45.3 | |

Test Example 4

Control Effect Against Bakanae Disease in Rice

Rice seeds (variety: Tanginbozu-dwarf) contaminated with benomyl-resistant Bakanae disease was mixed respectively with the granular wettable powder produced in Example 7 containing dinotefuran and benomyl as active ingredients, and with a commercially available seed disinfectant (BENLATE, trade name, a wettable powder containing benomyl as the active ingredient made by Sumitomo Chemical Co., Ltd.) as a control chemical, and a dressing treatment was carried out. After soaking the seeds (at 15° C. for three days) and forced sprouting (at 28° C. for one day), the seeds to which chemical treatment had been carried out were each sown at 100 seeds per plastic pot, and grown on in a greenhouse. The existence of disease onset was examined for all the seedlings with the naked eye at 20 days after sowing, and the disease onset seedling ratio was computed by the following Formula 4. Moreover, the existence or not of occurrences of phytotoxicity was also examined with the naked eye. Three replicates of the above test were performed, and the average values of the results are shown in Table 4.

Disease onset seedling ratio=(number of diseased seedlings/number of seeds sown)×100      Formula 4

TABLE 4

| Test compound | Active ingredient amount (g/kg seed) | Disease onset seedling ratio (%) | Phytotoxicity |
|---|---|---|---|
| Granular wettable powder of the invention (Example 7) | Dinotefuran 2.0 + Benomyl 5.0 | 29.4 | None |
| Control seed disinfectant BENLATE wettable powder | Benomyl 5.0 | 39.7 | None |
| No treatment | — | 45.3 | |

Test Example 5

Control Effect Against Beet Flea Beetle on Sugar Beet

Processing was carried out in a seed dressing machine (chemical liquid jetting within a rotating drum) using the wettable powders produced in Example 3, Example 4, Example 5, Reference Example 1 (comparative agent), Reference Example 2 (comparative agent), Reference Example 3 (comparative agent) and Reference Example 4 (comparative agent), and with Gaucho (trade name, an insecticide containing imidacloprid made by Bayer CropScience), at the following amounts of formulation per 100,000 seed unit of sugar beet seed.

Wettable powder: 65 g and 130 g of formulation/unit (one unit is 100,000 of sugar beet seeds).
Gaucho (imidacloprid): 130 g formulation/unit.
On the next day of treatment, the test seeds were sown at 50 seeds each, in a concrete pot filled with soil (5 m length×2 m width×60 cm depth).
The level of insect damage by striped flea beetle was investigated at 45 days after sowing and at 60 days after sowing, and the prevention index was computed by the following formula 5. Moreover, the existence or not of occurrences of phytotoxicity was also examined with the naked eye.
Results are shown in Table 5.
The index number levels of insect damage are as follows.
Index 0: No insect damage
Index 1: Slight level of insect damage
Index 2: Medium level of insect damage
Index 3: High level of insect damage Prevention index=100−((1×number of insect damage at index 1+2×number of insect damage at index 2+3×number of insect damage at index 3)/(3× total number of examinations)×100)      Formula 5

TABLE 5

| Test compound | Formulation treatment amount (g/unit) | Prevention index (%) | Phytotoxicity |
|---|---|---|---|
| Wettable powder of the invention (Example 3) | 65 g | 100 | None |
| | 130 g | 100 | None |
| Wettable powder of the invention (Example 4) | 65 g | 100 | None |
| | 130 g | 100 | None |
| Wettable powder of the invention (Example 5) | 65 g | 100 | None |
| | 130 g | 100 | None |
| Comparative wettable powder (Reference Example 1) | 65 g | 88 | None |
| | 130 g | 92 | None |
| Comparative wettable powder (Reference Example 2) | 65 g | 0 | None |
| | 130 g | 0 | None |
| Comparative wettable powder (Reference Example 3) | 65 g | 0 | None |
| | 130 g | 0 | None |
| Comparative wettable powder (Reference Example 4) | 65 g | 0 | None |
| | 130 g | 0 | None |
| Control insecticide Gaucho | 130 g | 85 | None |
| No treatment | — | 0 | None |

Test Example 6

Control Effect Against Adzuki Bean Weevil

Coating treatment was carried out using the respective flowables produced in Example 8, Example 9, Reference Example 5 (comparative agent), Reference Example 6 (comparative agent), and Reference Example 7 (comparative agent) at a dose of 5, 10 and 20 ml, with respect to 1 kg of azuki bean seed. After air-drying, portions thereof were moved to 9 cm deep petri dishes, and allowed to stand in a constant 25° C. temperature room. Two months and three months after the coating treatment, respectively, five male adult adzuki bean weevils and five adult female adzuki bean weeviles, ten in total, were grazed per deep petri dish. The number of de ad weevils and the number of eggs laid on the azuki beans were examined two days after grazing, and the mortality was computed by the following Formula 6. Five replicates of the above test were performed, and the average values of the results are shown in Table 6.

Mortality=(number of dead weevils in treated category/50 weevils)×100   Formula 6

B: Damage area is 5 to 10% of the surface area of root
C: Damage area is 2 to 4% of the surface area of root
D: Damage area is 1% of the surface area of root Degree of damage=(number of roots of A×4+number of roots of B×3+number of roots of C×2+number of roots of D×1+number of roots with no damage×0)/(number of roots examined×4)×100   Formula 7

TABLE 6

| Test compound | Active ingredient Amount (g/kg seed) | Two months after treatment Mortality % | Two months after treatment Number of eggs laid/female | Three months after treatment Mortality % | Three months after treatment Number of eggs laid/female |
|---|---|---|---|---|---|
| Flowable of the invention (Example 8) | Dinotefuran 1.0 + Flusulfamide 0.2 | 100 | 0.00 | 100 | 0.00 |
| | Dinotefuran 2.0 + Flusulfamide 0.4 | 100 | 0.00 | 100 | 0.00 |
| | Dinotefuran 4.0 + Flusulfamide 0.8 | 100 | 0.00 | 100 | 0.00 |
| Flowable of the invention (Example 9) | Dinotefuran 1.0 + Hymexazol 0.2 | 100 | 0.00 | 100 | 0.00 |
| | Dinotefuran 2.0 + Hymexazol 0.4 | 100 | 0.00 | 100 | 0.00 |
| | Dinotefuran 4.0 + Hymexazol 0.8 | 100 | 0.00 | 100 | 0.00 |
| Comparative Flowable (Reference Example 5) | Dinotefuran 1.0 | 95 | 0.06 | 93 | 0.10 |
| | Dinotefuran 2.0 | 98 | 0.02 | 94 | 0.08 |
| | Dinotefuran 4.0 | 100 | 0.00 | 100 | 0.00 |
| Comparative Flowable (Reference Example 6) | Flusulfamide 0.2 | 0 | 11.3 | 0 | 12.2 |
| | Flusulfamide 0.4 | 0 | 12.9 | 0 | 11.9 |
| | Flusulfamide 0.8 | 0 | 12.4 | 0 | 10.4 |
| Comparative Flowable (Reference Example 7) | Hymexazol 0.2 | 0 | 12.3 | 0 | 10.9 |
| | Hymexazol 0.4 | 0 | 12.1 | 0 | 12.0 |
| | Hymexazol 0.8 | 0 | 11.0 | 0 | 11.0 |
| No treatment | — | 0 | 11.5 | 0 | 10.8 |

Test Example 7

Control Effect Against Striped Flea Beetle

Soil surfaces were treated with commercially available formulations at amounts of:

STARKLE granule (trade name, a granular formulation containing 1% dinotefuran made by Sankyo Agro Co., Ltd.) at 9 kg/10 a;

NEBIJIN powder (trade name, a powder formulation containing 0.3% flusulfamide made by Sankyo Agro Co., Ltd.) at 30 kg/10 a;

MONGARIT granule (trade name, a granular formulation containing 1.5% simeconazole made by Sankyo Agro Co., Ltd.) at 6 kg/10 a;

STARKLE granule and NEBIJIN powder at 9 kg and 30 kg/10 a; and

STARKLE granule and MONGARIT granule at 9 kg and 6 kg/10 a, respectively, and the treated soils were lightly mixed with a rake.

Immediately after the soil treatment, Japanese radish seeds were sown in lines. The Japanese radishes were dug up at 32 days and at 52 days after sowing, respectively, and the damage level to the roots was examined on the following basis, and the degree of damage was computed from the following formula. Results are shown in Table 7.

Damage Level
A: Damage area is greater than 11% of the surface area of root

TABLE 7

| Test chemicals | Formulation amount | 32 days after treatment | 52 days after treatment |
|---|---|---|---|
| STARKLE granule | 9 kg/10 a | 30 | 20 |
| STARKLE granule + NEBIJIN powder | 9 kg/10 a + 30 kg/10 a | 20 | 13 |
| NEBIJIN powder | 30 kg/10 a | 65 | 80 |
| STARKLE granule + MONGARIT granule | 9 kg/10 a + 6 kg/10 a | 18 | 13 |
| MONGARIT granule | 6 kg/10 a | 65 | 88 |
| No treatment | — | 60 | 70 |

The invention claimed is:

1. A plant disease and insect damage control composition comprising active ingredients of (RS)-1-methyl-2-nitro-3-(tetrahydro-3-furylmethyl)guanidine (common name: dinotefuran) and at least one fungicidal compound selected from the group consisting of 2',4-dichloro-α,α,α-trifluoro-4'-nitro-m-toluenesulfonanilide (common name: flusulfamide), 3-hydroxy-5-methylisoxazol (common name: hymexazol), and (RS)-2-(4-fluorophenyl)-1-(1H-1,2,4-triazol-1-yl)-3-(trimethylsilyl)propan-2-ol (common name: simeconazole).

2. The plant disease and insect damage control composition according to claim 1, wherein the at least one fungicidal compound comprises 2',4-dichloro-α,α,α-trifluoro-4'-nitro-m-toluenesulfonanilide (common name: flusulfamide).

3. The plant disease and insect damage control composition according to claim 1, wherein the at least one fungicidal compound comprises 3-hydroxy-5-methylisoxazol (common name: hymexazol).

4. The plant disease and insect damage control composition according to claim 1, wherein the at least one fungicidal compound comprises (RS)-2-(4-fluorophenyl)-1-(1H-1,2,4-triazol-1-yl)-3-(trimethylsilyl)propan-2-ol (common name: simeconazole).

5. The plant disease and insect damage control composition according to claim 1, wherein the at least one fungicidal compound comprises a mixed composition of at least two selected from the group consisting of flusulfamide, hymexazol, and simeconazole.

6. A plant disease and insect damage control method comprising applying the pest control composition according claim 1 to a plant body, soil, plant seed, stored cereal, stored legume, stored fruit, stored vegetable, silage, stored flowering plant, or export/import timber.

7. The plant disease and insect damage control method according to claim 6, wherein the method of application to plant seeds is spray treatment, coating treatment, dip treatment, or dressing treatment of seeds.

8. The plant disease and insect damage control method according to claim 6, wherein the method of application to a stored cereal, stored legume, stored fruit, stored vegetable, silage, stored flowering plants, or export/import timber is spray treatment, coating treatment, dip treatment, dressing treatment, fumigation treatment, smoke treatment, or pressure injection.

9. Plant seed, stored cereal, stored legume, stored fruit, stored vegetable, silage, stored flowering plant, or export/import timber to which the plant disease and insect damage control composition according to claim 1 has been applied.

10. The plant disease and insect damage control method according to claim 6, wherein the method of application to a plant body or soil is foliar application to a plant body, spray treatment to the soil surface, soil incorporation after spray treatment to the soil surface, injection treatment into the soil, or soil drenching treatment.

11. A method of controlling plant disease and insect damage to a plant body grown from a plant seed, the method comprising applying, to the plant seed, the plant disease and insect damage control composition according to claim 1.

* * * * *